(12) United States Patent
Conger et al.

(10) Patent No.: US 8,399,537 B2
(45) Date of Patent: *Mar. 19, 2013

(54) COMPOSITIONS AND METHODS FOR NAIL COATINGS

(75) Inventors: Chad Conger, San Marcos, CA (US); Thong Vu, Vista, CA (US)

(73) Assignee: Creative Nail Design, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/079,261

(22) Filed: Apr. 4, 2011

(65) Prior Publication Data

US 2011/0182838 A1    Jul. 28, 2011

Related U.S. Application Data

(63) Continuation of application No. 12/555,571, filed on Sep. 8, 2009, now Pat. No. 8,263,677.

(51) Int. Cl.
*C08F 20/18* (2006.01)
*A61L 27/56* (2006.01)
*C08J 3/09* (2006.01)
*A45D 31/00* (2006.01)

(52) U.S. Cl. ............... 522/182; 522/49; 522/90; 522/96; 522/120; 522/121; 424/61; 424/401; 521/149

(58) Field of Classification Search .......... 521/149; 424/61, 401; 523/105; 522/64, 49, 90, 96, 522/120, 121

See application file for complete search history.

(56) References Cited

U.S. PATENT DOCUMENTS

| | | | |
|---|---|---|---|
| 1,548,497 A | 8/1925 | Weeks |
| 1,743,922 A | 1/1930 | Kirlin |
| 1,900,761 A | 3/1933 | Proteau |
| 1,947,153 A | 2/1934 | Dellinger |
| 2,979,061 A | 4/1961 | Greenman |
| 3,297,664 A | 1/1967 | Miskel |
| 3,629,187 A | 12/1971 | Waller |
| 3,709,866 A | 1/1973 | Waller |
| 3,928,113 A | 12/1975 | Rosenberg |
| 4,089,763 A | 5/1978 | Dart |
| 4,158,053 A | 6/1979 | Greene et al. |
| 4,174,307 A | 11/1979 | Rowe |
| 4,189,365 A | 2/1980 | Schmitt |
| 4,205,018 A | 5/1980 | Nagasawa |
| 4,229,431 A | 10/1980 | Lee, Jr. |
| 4,260,701 A | 4/1981 | Lee, Jr. |
| 4,421,881 A | 12/1983 | Benkendorf |
| 4,424,252 A | 1/1984 | Nativi |
| 4,514,527 A | 4/1985 | Bowen |
| 4,521,550 A | 6/1985 | Bowen |
| 4,572,888 A | 2/1986 | Maeda |
| 4,574,138 A | 3/1986 | Moran, Jr. |
| 4,596,260 A | 6/1986 | Giuliano |
| 4,600,030 A | 7/1986 | Newman |
| 4,666,952 A | 5/1987 | Henne |
| 4,682,612 A | 7/1987 | Giuliano |
| 4,690,369 A | 9/1987 | Giuliano |
| 4,692,396 A | 9/1987 | Uchida |
| 4,704,303 A | 11/1987 | Cornell |
| 4,718,957 A | 1/1988 | Sensenbrenner |
| 4,721,735 A | 1/1988 | Bennett |
| 4,745,003 A | 5/1988 | Sirkoch |
| 4,766,005 A | 8/1988 | Montgomery |
| 4,775,580 A | 10/1988 | Dighton |
| 4,813,875 A | 3/1989 | Hare |
| 4,844,102 A | 7/1989 | Repensek |
| 4,846,165 A | 7/1989 | Hare |
| 4,863,993 A | 9/1989 | Montgomery |
| 4,867,680 A | 9/1989 | Hare |
| 5,026,780 A | 6/1991 | Takizawa |
| 5,063,257 A | 11/1991 | Akahane |
| 5,071,888 A | 12/1991 | Kubota |
| 5,118,495 A | 6/1992 | Nafziger |
| 5,127,414 A | 7/1992 | Mast |
| 5,173,288 A | 12/1992 | Everhart et al. |
| 5,177,120 A | 1/1993 | Hare |
| 5,194,292 A | 3/1993 | Billings |
| 5,206,011 A | 4/1993 | Pappas |
| 5,219,965 A | 6/1993 | Valint, Jr. |
| 5,229,431 A | 7/1993 | Pinchuk |
| 5,270,351 A | 12/1993 | Bowen |
| 5,314,683 A | 5/1994 | Schlossman |
| 5,328,725 A | 7/1994 | Sato |
| 5,338,769 A | 8/1994 | Miyamoto |
| 5,344,583 A | 9/1994 | Bayless |

(Continued)

FOREIGN PATENT DOCUMENTS

EP  0356868  3/1990
EP  0453628  10/1991

(Continued)

OTHER PUBLICATIONS

Data Sheet for Diurethane Dimethacrylate from Esstech, Inc. 2011.*

(Continued)

*Primary Examiner* — Randy Gulakowski
*Assistant Examiner* — Kara Boyle
(74) *Attorney, Agent, or Firm* — Venable LLP; Keith G. Haddaway; Lars H. Genieser

(57) ABSTRACT

The present disclosure relates generally to compositions for natural and artificial nail coatings, and particularly, but not by way of limitation, to polymerizable compositions and adhesion-promoting basecoats polymerized therefrom. The disclosure further relates to methods of making a polymerized basecoat that are more easily removed than artificial nail enhancements and more durable and long lasting than nail polish coatings.

25 Claims, No Drawings

U.S. PATENT DOCUMENTS

| | | | |
|---|---|---|---|
| 5,407,666 | A | 4/1995 | Patel |
| 5,415,903 | A | 5/1995 | Hoffman |
| 5,424,061 | A | 6/1995 | Pappas |
| 5,426,166 | A | 6/1995 | Usifer |
| 5,435,994 | A | 7/1995 | Valenty |
| 5,453,451 | A | 9/1995 | Sokol |
| 5,456,905 | A | 10/1995 | Valenty |
| 5,484,864 | A | 1/1996 | Usifer |
| 5,516,509 | A | 5/1996 | Marr-Leisy |
| 5,637,292 | A | 6/1997 | Thomas |
| 5,662,891 | A | 9/1997 | Martin |
| 5,690,940 | A | 11/1997 | Joo |
| 5,698,371 | A | 12/1997 | Mirle |
| 5,708,052 | A | 1/1998 | Fischer |
| 5,720,804 | A | 2/1998 | Martin |
| 5,785,958 | A * | 7/1998 | Sirdesai et al. ........... 424/61 |
| 5,792,447 | A | 8/1998 | Socci |
| 5,824,373 | A | 10/1998 | Biller |
| 5,849,853 | A | 12/1998 | Schade |
| 5,871,573 | A | 2/1999 | Cook et al. |
| 5,958,951 | A | 9/1999 | Ahrndt |
| 5,965,111 | A | 10/1999 | Ellingson |
| 5,965,147 | A | 10/1999 | Steffier |
| 5,985,951 | A * | 11/1999 | Cook ..................... 522/88 |
| 5,985,998 | A | 11/1999 | Sommerfeld |
| 5,994,530 | A | 11/1999 | Posey-Dowty |
| 5,998,495 | A | 12/1999 | Oxman |
| 6,015,549 | A | 1/2000 | Cowperthwaite |
| 6,020,402 | A | 2/2000 | Anand |
| 6,121,381 | A | 9/2000 | Deguchi |
| 6,147,137 | A * | 11/2000 | Jia ..................... 523/118 |
| 6,238,679 | B1 | 5/2001 | delaPoterie |
| 6,239,189 | B1 | 5/2001 | Narayan |
| 6,251,520 | B1 | 6/2001 | Blizzard et al. |
| 6,254,878 | B1 | 7/2001 | Bednarek et al. |
| 6,255,034 | B1 | 7/2001 | Shimada |
| 6,355,599 | B1 | 3/2002 | Zahora |
| 6,391,938 | B1 | 5/2002 | Lilley |
| 6,413,696 | B1 | 7/2002 | Pang |
| 6,426,034 | B1 | 7/2002 | McComas |
| 6,481,444 | B1 | 11/2002 | Lilley |
| 6,599,958 | B2 | 7/2003 | Lilley |
| 6,685,838 | B2 | 2/2004 | Licata |
| 6,750,277 | B1 | 6/2004 | Yamana |
| 6,803,394 | B2 | 10/2004 | Lilley |
| 6,818,207 | B1 | 11/2004 | Schoon |
| 6,831,115 | B2 | 12/2004 | Williams |
| 6,939,551 | B2 * | 9/2005 | Amato et al. ........... 424/401 |
| 7,063,936 | B2 | 6/2006 | Kakino |
| 7,098,256 | B2 | 8/2006 | Ong |
| 7,125,591 | B2 | 10/2006 | Nakajima et al. |
| 7,309,550 | B2 | 12/2007 | Rach |
| 7,364,834 | B2 | 4/2008 | Barr |
| 7,378,460 | B2 | 5/2008 | Schmidt |
| 7,388,039 | B2 | 6/2008 | Williams |
| 7,514,477 | B2 | 4/2009 | Klare |
| 7,595,351 | B2 | 9/2009 | Hayes |
| 7,615,283 | B2 | 11/2009 | Radcliffe |
| 7,649,058 | B2 | 1/2010 | McCabe |
| 7,713,680 | B2 | 5/2010 | Ito |
| 7,718,264 | B2 | 5/2010 | Klun |
| 7,722,939 | B2 | 5/2010 | Schwantes |
| 7,806,050 | B2 | 10/2010 | Nakamura |
| 2001/0007676 | A1* | 7/2001 | Mui et al. ........... 424/401 |
| 2002/0156144 | A1 | 10/2002 | Williams |
| 2003/0019501 | A1* | 1/2003 | Hirota et al. ........... 132/73 |
| 2003/0134932 | A1 | 7/2003 | Lehmann |
| 2003/0175225 | A1* | 9/2003 | Leacock et al. ........... 424/61 |
| 2003/0220416 | A1 | 11/2003 | Montgomery |
| 2004/0249014 | A1 | 12/2004 | Williams |
| 2005/0002878 | A1 | 1/2005 | Lefrancois et al. |
| 2006/0005772 | A1 | 1/2006 | Shin |
| 2006/0039939 | A1 | 2/2006 | Lai |
| 2006/0128833 | A1 | 6/2006 | Itoh et al. |
| 2006/0189728 | A1 | 8/2006 | Qian |
| 2007/0021533 | A1 | 1/2007 | Yan |
| 2007/0099119 | A1 | 5/2007 | Rach |
| 2007/0106017 | A1 | 5/2007 | Kessel |
| 2008/0149270 | A1 | 6/2008 | Oshima |
| 2008/0167399 | A1 | 7/2008 | Utterodt |
| 2008/0213506 | A1 | 9/2008 | Eu |
| 2008/0241083 | A1 | 10/2008 | Schoon |
| 2009/0086492 | A1 | 4/2009 | Meyer |
| 2009/0220436 | A1 | 9/2009 | Anderson et al. |
| 2010/0012263 | A1 | 1/2010 | Oshima |
| 2010/0105289 | A1 | 4/2010 | Yonezu |
| 2011/0045036 | A1 | 2/2011 | Lintner et al. |

FOREIGN PATENT DOCUMENTS

| | | |
|---|---|---|
| EP | 0426085 | 5/1992 |
| EP | 0545116 | 6/1993 |
| EP | 943310 | 3/2002 |
| EP | 1479364 | 11/2004 |
| EP | 1450755 | 8/2008 |
| GB | 656264 | 8/1951 |
| JP | 5271460 | 10/1993 |
| KR | 970002606 | 3/1997 |
| WO | 9312759 | 7/1993 |
| WO | 9848769 | 11/1998 |
| WO | 9955290 | 11/1999 |
| WO | 0236637 | 5/2002 |
| WO | 2004030801 | 4/2004 |
| WO | 2008082929 | 7/2008 |
| WO | 2009005975 | 1/2009 |
| WO | 2011011304 | 1/2011 |

OTHER PUBLICATIONS

Cheremisinoff, N.P. "Handbook of Hazardous Chemical Properties," Copyright 2000, Elsevier, p. 211.

International Search Report for PCT International Application No. PCT/US2010/147171, mailed Nov. 10, 2010.

Kumar, Sudesh G, et al., Biodegradation of gelatin-g-Poly (ethyl Acrylate) copolymers, 26 Journal of Applied Polymer Science, (1981) 3633-3641.

Physical Properties of Monomers, "Diurethane Dimethacrylate (isomers)." Polymer Handbook, 4th Edition, 1999, John Wiley & Sons.

Venz S. et al., Modified Surface-Active Monomers for Adhesive Binding to Dentin, vol. 72, No. 3 Journal of Dental Research, Mar. 1993, pp. 582-586.

International Search Report for PCT International Application No. PCT/US2011/027455, mailed May 9, 2011.

International Search Report for PCT International Application No. PCT/US2010/047165, mailed Feb. 25, 2011.

International Search Report for PCT International Application No. PCT/US2010/047169, mailed Nov. 9, 2010.

Data Sheet for Polypropylene Glycol Monomethacrylate. Sartomer. 2011.

Ebecryl 200 Data Sheet. Lookchem. 2008.

International Preliminary Report on Patentability issued in International Application No. PCT/US2010/047169 dated Apr. 11, 2012.

International Preliminary Report on Patentability issued in International Application No. PCT/US2010/074165 dated Mar. 13, 2012.

International Preliminary Report on Patentability issued in International Application No. PCT/US2010/074171 dated Apr. 11, 2012.

Office Action issued in U.S. Appl. No. 12/555,571 dated May 17, 2011.

Office Action issued in U.S. Appl. No. 12/555,571 dated Oct. 26, 2011.

Office Action issued in U.S. Appl. No. 12/573,633 dated Feb. 13, 2012.

Office Action issued in U.S. Appl. No. 12/573,633 dated May 24, 2011.

Office Action issued in U.S. Appl. No. 12/573,640 dated Aug. 15, 2012.

Office Action issued in U.S. Appl. No. 13/303,584 dated Oct. 22, 2012.

* cited by examiner

COMPOSITIONS AND METHODS FOR NAIL COATINGS

PARENT CASE TEXT

The present application is a continuation of application Ser. No. 12/555,571, filed Sep. 8, 2009, the entire content of which is incorporated by reference for all purposes. The entire contents of co-pending application Ser. No. 12/573,633, filed Oct. 5, 2009, of co-pending application Ser. No. 12/573,640, filed Oct. 5, 2009, and of U.S. Pat. No. 6,818,207, assigned to the assignee of the present invention are each incorporated by reference in their entirety and for all purposes.

FIELD OF THE INVENTION

The present disclosure relates generally to compositions for nail coatings, and particularly, but not by way of limitation, to polymerizable compositions and adhesion-promoting basecoats polymerized therefrom.

BACKGROUND

The information provided below is not admitted to be prior art to the present invention, but is provided solely to assist the understanding of the reader.

Artificial fingernail and toenail compositions in the form of nail coatings and enhancements are well known and have become a major product line in the appearance and beauty industry. The appearance of one's fingernails (and in many cases also toenails) has become of importance to many fashion conscious individuals or those who wish to correct physical deformities to the natural nail. Commercial artificial nail compositions have been used to enhance the appearance of nails and also to enhance the physical properties of nails, including strengthening fragile nail plates.

Conventional nail coatings may be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of long lasting, highly durable cross-linked thermoset nail coating that is difficult to remove. Artificial nails may possess greatly enhanced adhesion, durability, as well as scratch and solvent resistance when compared to nail polishes. However, because of these inherent properties, such thermosets are much harder to remove, should the consumer so desire. Removal typically requires soaking in non-reactive solvents for 30-90 minutes (for acrylics and currently available "soakable gels"; it may take more than 90 minutes if ever to remove traditional UV nail gels by solvent) and typically may also require heavily abrading the surface or scraping with a wooden or metal probe to assist the removal process.

There remains a need for a cosmetic product that possesses the enhanced adhesion properties and durability of thermosets, yet also possesses the ease of removal more similar to that of nail polishes.

The present disclosure forms part of a nail coating system comprising a reactive basecoat adhesion layer (the present disclosure, application Ser. No. 12/555,571) an intermediate, decorative and reactive color layer (application Ser. No. 12/573,633), and a protective and reactive topcoat (application Ser. No. 12/573,640). The contents of each application are mutually incorporated into each of the others by reference for all purposes.

Other objects and advantages will become apparent from the following disclosure.

SUMMARY OF INVENTION

An aspect of the present disclosure provides a nail coating comprising a 3-dimensional (3-D) thermoset lattice interpenetrated by a network comprising an organic solvent-dissolvable resin. According to an aspect of the disclosure, a 3-D thermoset lattice provides the enhanced adhesion, durability/toughness, of conventional artificial nail coatings. According to an aspect of the disclosure, an interconnected system of voids and an interpenetrating network of an organic solvent-dissolvable resin provides ease of solvent removability as compared to conventional nail enhancements.

According to an aspect, the present disclosure provides a liquid composition comprising at least one monomer, and/or oligomer, and/or polymer which polymerize to a 3-D thermoset. According to an aspect, the present disclosure provides a liquid composition comprising at least one organic solvent-dissolvable resin. According to an aspect, the organic solvent-dissolvable resin forms a network of inclusions within the 3-D thermoset lattice.

According to an aspect, the present disclosure provides a liquid composition comprising at least one polymer which is incorporated within the 3-D lattice and which conveys enhanced adhesion and which facilitates solvent "unzipping" of the polymerized lattice. According to an aspect, the polymer which conveys both enhanced adhesion and which facilitates solvent removal of the polymer is a polymer co-polymerized from methyl methacrylate (MMA) and methacrylic acid (MAA) to form a polymer composed of polymethyl methacrylate (PMMA) and polymethacrylic acid (PMAA). According to an aspect, the monomeric portions of the polymer are present in a ratio of 90 parts PMMA to 10 parts PMAA (90:10 PMMA/PMAA). According to an aspect, the MAA monomer fraction may vary from 0 to 100%.

According to an aspect, the present disclosure provides a monomer which confers the "unzipping" property of ease of removal of the polymerized lattice. According to an aspect, the monomer may be polypropylene glycol-4-monomethacrylate (PPG4 monomethacrylate). According to an aspect, suitable monomers may include any acrylated or methacrylated monomer in the PPG family. According to an aspect, the "unzipping" monomers are present at from about 0 to about 70 weight % (wt %).

According to an aspect, the liquid composition comprises reactive monomers, and/or oligomers, and/or polymers which provides the polymerized composition increased adhesiveness. According to an aspect, such reactive monomers, and/or oligomers, and/or polymers may be a (meth)acrylate. As is known to persons of skill in the polymer arts, the term (meth)acrylate encompasses acrylates and/or methacrylates. According to an aspect, such reactive monomers, and/or oligomers, and/or polymers may be selected from the group consisting of hydroxyethylmethacrylate (HEMA), hydroxypropylmethacrylate (HPMA), Ethyl Methacrylate (EMA), Tetrahydrofurfuryl Methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof. According to an aspect, such reactive monomers, and/or oligomers, and/or polymers possess acidic functionality. According to an aspect, the monomer, oligomer or polymer which provides the polymerized composition increased adhesiveness is present from about 0 to about 80 wt %.

An aspect of the present disclosure provides a polymerizable liquid composition comprising a non-reactive, solvent-dissolvable, film-forming polymer. According to an aspect, the non-reactive, solvent-dissolvable, film-forming polymer is a cellulose ester. According to a particular aspect, the non-reactive, solvent-dissolvable, film-forming polymer is a cellulose acetate alkylate. According to a more particular aspect, the non-reactive, solvent-dissolvable, film-forming polymer is a cellulose acetate butyrate or a cellulose acetate propionate. According to a further aspect, the ingredient which provides for ease of removal may be present at from about 0 to about 50 wt %.

An aspect of the present disclosure provides a method of removal. According to an aspect, the thermoset polymerized from the disclosed composition is provided sensitivity to organic solvents and, in particular, to acetone. According to an aspect of the disclosure, means are provided to distribute organic solvent to the polymer/natural nail interface. According to an aspect, delivering an appropriate solvent to the polymer/natural nail interface will result in an unzipping effect which leads to rapid disruption of the adhesive bond interface and greatly facilitates quick and gentle removal from the natural nail.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BRIEF DESCRIPTION OF DRAWINGS

Not Applicable.

DETAILED DESCRIPTION OF A PREFERRED EMBODIMENT

Nail coatings commonly consist of a material applied to a keratin nail surface. Prior art coatings may damage the nail by at least two mechanisms. First, adequate adhesion of the enhancement to the nail may require abrasion to roughen the nail surface. And second, removal of the enhancement may require prolonged exposure to possibly damaging solvents and or further abrasion of the nail surface.

An embodiment of the present disclosure provides a nail coating comprising a 3-dimensional (3-D) thermoset lattice interpenetrated by a network comprising an organic solvent-dissolvable resin. According to an aspect of the disclosure, a 3-D thermoset lattice provides the enhanced adhesion, toughness, and scratch-resistance of conventional artificial nails.

An embodiment of the liquid composition comprises reactive monomers, and/or oligomers, and/or polymers which provides the polymerized composition increased adhesiveness. In certain embodiments, such reactive monomers, and/or oligomers, and/or polymers may be a (meth)acrylate. As is known to persons of skill in the polymer arts, the term (meth)acrylate encompasses acrylates and/or methacrylates. According to an aspect, such reactive monomers, and/or oligomers, and/or polymers may be selected from the group consisting of hydroxypropyl methacrylate (HPMA), hydroxyethyl methacrylate (HEMA), EMA, THFMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof According to an aspect, such reactive monomers, and/or oligomers, and/or polymers possess acidic functionality. According to an aspect, the monomer, oligomer or polymer which provides the polymerized composition increased adhesiveness is present from about 0 to about 50 wt %.

Certain embodiments of the liquid composition comprise at least one polymer which is incorporated within the 3-D lattice and which conveys enhanced adhesiveness and which facilitates solvent "unzipping" of the polymerized lattice. The inventors have discovered that the presence of certain polymers at the polymer/natural nail interface, renders the interfacial bonds susceptible to rupture by organic solvents.

According to an aspect, a polymer which conveys both enhanced adhesiveness and which sensitizes the polymer/nail interface to solvent is a co-polymer of polymethyl methacrylate (PMMA) and polymethacrylic acid (PMAA). According to an aspect, the monomers are present in the polymer in a ratio of 90 parts PMMA to 10 parts PMAA (90:10 PMMA/PMAA). According to an aspect, the PMAA monomer fraction may vary from 0 to 100%. According to an aspect, the PMMA-PMAA copolymer has a PMMA:PMAA monomer ratio of about 50:50. According to an aspect, the PMMA-PMAA copolymer has a PMMA:PMAA monomer ratio of about 60:40. According to an aspect, the PMMA-PMAA copolymer has a PMMA:PMAA monomer ratio of about 80:20. According to an aspect, the PMMA-PMAA copolymer has a PMMA:PMAA monomer ratio of about 90:10. According to an aspect, the PMMA-PMAA copolymer has a PMMA:PMAA monomer ratio of about 95:5.

Certain embodiments of the liquid composition comprise at least one monomer which confers the "unzipping" property by imparting to the interfacial bonds a high degree of sensitivity to organic solvent. According to an aspect, the at least one monomer may be polypropylene glycol-4-monomethacrylate (PPG-4 monomethacrylate). According to an aspect, suitable monomers may include any acrylated or methacrylated monomer in the PPG or polyethylene glycol (PEG) family. According to an aspect, the "unzipping" monomers are present at from about 0 to about 70 weight % (wt %).

An embodiment of the present disclosure provides a polymerizable liquid composition comprised of an aromatic or aliphatic (meth)acrylate monomer which provides improved adhesion, viscosity, wear and durability. In certain embodiments, the (meth)acrylate monomer is a tetrahydrofurfuryl methacrylate. In other embodiments, some or all of the tetrahydrofurfuryl methacrylate may be substituted by such monomers including, but not limited to methyl or ethyl methacrylate, hydroxypropyl or hydroxybutyl methacrylate, and/or other monomers such as pyromellitic dianhydride glyceryl dimethacrylate, and similar (meth)acrylate monomers. The aromatic or aliphatic (meth)acrylate monomer may be present from about 0 to about 70 wt %.

Certain embodiments of the present disclosure may comprise another or "second" aromatic or aliphatic (meth)acrylate monomer which may be present to improve adhesion. The second (meth)acrylate monomer may be a pyromellitic dianhydride glyceryl dimethacrylate (PMGDM). In general, the second methacrylate monomer may be an acid-functional, (meth)acrylate monomer. The second methacrylate monomer may be present from about 0 to about 70 wt %.

Certain embodiments of the polymerizable liquid composition of the present disclosure may comprise a urethane (meth)acrylate resin which may convey flexibility and toughness to the polymerized product. In certain embodiments, urethane methacrylates are preferred. The urethane (meth)acrylate monomer may be present from about 0 to about 80 wt %. In certain embodiments, the urethane (meth)acrylate may have a molecular weight (grams/mole) of from about 100 to about 20,000. In certain embodiments, the urethane (meth)acrylate may have a molecular weight of from about 300 to about 15,000. In certain embodiments, the urethane (meth)acrylate may have a molecular weight of from about 500 to about 13,000. In certain embodiments, the urethane (meth)acrylate may have a molecular weight of from about 500 to about 6,000.

In certain embodiments of the disclosure, the 3-D thermoset lattice is interpenetrated by a network of voids left by the evolution of a solvent. During the curing process, domains of a non-reactive, organic solvent-dissolvable resin form within the crosslinked polymer matrix. When it is desired to remove the nail covering, the polymer is exposed to a solvent which penetrates the network of voids to the domains of the solvent-dissolvable resin. Dissolution of the resin allows further penetration of solvent to the interior of the thermoset and also to the polymer/nail interface.

Certain embodiments of the polymerizable liquid composition of the present disclosure may comprise a non-reactive, solvent-dissolvable, film-forming polymer. According to an aspect, the non-reactive, solvent-dissolvable, film-forming polymer is a cellulose ester. According to a particular aspect, the non-reactive, solvent-dissolvable, film-forming polymer is a cellulose acetate alkylate. According to a more particular aspect, the non-reactive, solvent-dissolvable, film-forming polymer is a cellulose acetate butyrate or a cellulose acetate propionate. The non-reactive, solvent-dissolvable, film-forming polymer may be a mixture of any acceptable polymer. According to a further aspect, the non-reactive, solvent-dissolvable, film-forming polymer may be present at from about 0 to about 50 wt %.

Without being bound by theory, the present disclosure eases removal of the nail covering by facilitating entrance of solvent into the interior of the coating. Conventional polymerized nail coatings are weakened by long-term (30 to 90 minute) exposure to organic solvents. The solvent slowly seeps in at the outer surface and edges of the thermoset and eventually swells the coating. The swelling eventually weakens the entire matrix structure, as well as disrupts adhesion to the nail surface. Even a weakly attached nail coating may require surface abrasion to enhance solvent penetration and speed removal. However, the slow rate at which solvent diffuses through the thermoset, limits the rate of swelling and subsequent removal.

The present invention provides a 3-D thermoset interpenetrated by a network of voids left from evolution of solvent during cure and domains of organic solvent-soluble polymer. When the coating is exposed to organic solvents, the solvents penetrate the bulk material through the voids left during the curing process to the cellulose ester, or other non-reactive, organic solvent-soluble polymer, which is dissolved by the solvent, leaving further voids which allow deeper and more complete penetration into the bulk of the material down to the polymer/nail interface. The result is a series of solvent accessible passageways riddled throughout the thermoset. Under these conditions, solvent may attack the interior of the thermoset no longer limited by a slow diffusion rate.

The present disclosure provides a basecoat as a layer intermediate between the nail and coating surfaces. The inventive basecoat is a polymerizable liquid so as to provide a completely conformal coating over the nail surface. The inventive composition may be polymerizable with actinic radiation. The actinic radiation may be ultraviolet (UV) radiation.

The inventive composition comprises monomers and oligomers having a plurality of free hydroxyl groups. The hydroxyl groups of the inventive composition may be available to form hydrogen bonds with a substrate which may be a keratinous nail surface. The hydroxyl groups of the inventive composition may be available to form hydrogen bonds with a substrate which may be a surface of a natural nail or artificial nail enhancement coating.

After the liquid composition is applied to a nail surface, the liquid is polymerized or cured. The liquid composition comprises ethylenic unsaturated (meth)acrylates which may be polymerized or cured by a UV-initiated, free-radical polymerization method. Persons of skill in the polymerization arts may readily determine suitable photoinitiators for use with the invention. Set forth below are, non-limiting representative photoinitiators that are suitable for purposes of the invention.

A non-limiting suitable photoinitiator is 2,4,6-trimethylbenzoyldiphenylphosphinate, which may be obtained under the tradename Lucirin® TPO-L (BASF Aktiengesellschaft, Ludwigshafen, DE). The 2,4,6-trimethylbenzoyldiphenylphosphinate photoinitiator may be present from about 0% to about 10 wt %.

A non-limiting suitable photoinitiator is hydroxycyclohexyl phenyl ketone, which may be obtained under the tradename Irgacure® 184 and which may be present from about 0 to about 10 wt %.

A non-limiting suitable photoinitiator is benzil dimethyl ketal (BDK), which may be obtained under the tradename FIRSTCURE® BDK (Albemarle, Baton Rouge, La., US) and which may be present from about 0 to about 10 wt %.

A conventional thermoset nail coating comprises 100% solids and does not comprise non-reactive solvents. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. A particularly suitable solvent is acetone. Typically a solvent or a mixture of solvents is included at up to about 70 weight percent.

Certain embodiments of the formulation may optionally comprise (meth)acrylate monomers or polymers in order to fine tune adhesion and removal properties. Non-limiting examples of such (meth)acrylates include: mono or poly (meth)acrylic acids, HPMA, HEMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, ethyl methacrylate, tetrahydrofurfuryl methacrylate, butyl methacrylate, isobutyl methacrylate, PEG-4 dimethacrylate, PPG monomethacrylate, trimethylolpropane trimethacrylate, hydroxyethyl methacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxy methacrylate.

Certain embodiments of the formulation may optionally comprise resins, such as, but not limited to polyvinylbutyral and/or tosylamide formaldehyde resins. Such resins act as film formers, adhesion promoters, and aids to removal. These resins may also qualify as solvent-dissolvable, interpenetrating resins which can be extracted to create channels for solvent absorption and migration.

The unpolymerized basecoat may have the consistency of a liquid or gel. The unpolymerized basecoat may be applied to a keratin nail surface. The unpolymerized basecoat may be polymerized by exposure to UV radiation. In an embodiment the unpolymerized basecoat may be applied to a nail surface and contacted with a color layer such as is described in co-pending (application Ser. No. 12/573,633). The nail surface-basecoat-color layer system may be exposed to UV radiation. The basecoat may be polymerized thereby adhering the color layer to the nail surface.

In an embodiment, the basecoat is applied without abrading the nail surface. In an embodiment, a color layer or other material may be adhered to the nail surface without abrading the nail surface. In an embodiment, a color layer or other material may be removed from the nail surface without abrading the surface of the nail coating.

As compared to conventional artificial nail enhancement coatings, the present disclosure relates to a major advantage in that it enables the tough, rubbery color layer to adhere to the natural nail for periods in excess of two weeks without adhesion loss or other signs of breakdown of the coating. In contrast to conventional coatings, the present disclosure relates to a UV gel system that is less damaging to the nail, since the application process requires no abrasive filing of the natural nail. And the process of removal at most calls for the use of a light touch of a wooden stick. The present basecoat is removable without any abrasion of the uppermost layers if they are solvent-removable themselves. Moreover, in comparison to conventional systems, the present disclosure relates to a more rapidly removable basecoat system achieving removal in 20 seconds for basecoat alone to 20 minutes for the whole system.

Polymerizable basecoats may adhere to the keratin nail surface by means of hydrogen and/or covalent bonds. The basecoat may be removed from the nail surface by means of organic solvents. Non-limiting solvents include acetone, butyl acetate, isopropyl alcohol, ethanol, ethyl acetate, methyl acetate, methyl ethyl ketone, and mixtures thereof.

INDUSTRIAL UTILITY

This invention has industrial applicability in providing compositions and methods for improving the adhesion of nail coatings to natural nails without requiring abrasion of the natural nail. The invention further provides means for removing a nail coating without requiring extended soak times or abrasion of the natural nail surface.

The invention claimed is:
1. A system for covering a nail surface comprising:
    a coating curable to an acrylic thermoset lattice layer conforming over the nail surface upon exposure to actinic radiation,
    wherein the coating comprises
    a polymerizable (meth)acrylate,
    a polypropylene glycol (meth)acrylated monomer or polyethylene glycol (meth)acrylated monomer,
    a non-reactive solvent, and
    a non-reactive, solvent-dissolvable polymer.
2. The nail covering system of claim 1, wherein said non-reactive, solvent-dissolvable polymer is selected from the group consisting of: cellulose esters, polyvinylbutyral resins, tosylamide (toluensulfonamide) formaldehyde resins, and mixtures thereof.
3. The nail covering system of claim 2, wherein said cellulose ester is selected from the group consisting of cellulose acetate butyrate, cellulose acetate propionate, and mixtures thereof.
4. The nail covering system of claim 1, further comprising an adhesion promoter.
5. The nail covering system of claim 4, wherein said adhesion promoter is selected from the group consisting of:
    hydroxypropyl methacrylate (HPMA),
    hydroxyethyl methacrylate (HEMA),
    ethyl methacrylate (EMA),
    tetrahydrofurfuryl methacrylate THFMA,
    pyromellitic dianhydride di(meth)acrylate,
    pyromellitic dianhydride glyceryl dimethacrylate (PMGDM),
    pyromellitic dimethacrylate,
    methacroyloxyethyl maleate,
    2-hydroxyethyl methacrylate/succinate,
    1,3-glycerol dimethacrylate/succinate adduct,
    phthalic acid monoethyl methacrylate,
    methacroyloxyethyl maleate,
    2-hydroxyethyl methacrylate/succinate,
    1,3-glycerol dimethacrylate/succinate adduct,
    butyl methacrylate,
    isobutyl methacrylate,
    PEG-4 dimethacrylate,
    PPG monomethacrylate,
    trimethylolpropane trimethacrylate,
    isopropylidenediphenyl bisglycidyl methacrylate,
    lauryl methacrylate,
    cyclohexyl methacrylate,
    hexyl methacrylate,
    urethane methacrylate,
    triethylene glycol dimethacrylate,
    ethylene glycol dimethacrylate,
    tetraethylene glycol dimethacrylate,
    trimethylolpropane trimethacrylate,
    neopentylglycol dimethacylate,
    acetoacetoxy methacrylate,
    hydroxybutylmethacrylate,
    acetoacetoxyethylmethacrylate (AAEMA),
    and mixtures thereof.
6. The nail covering system of claim 1, further comprising at least one PMMA-PMAA copolymer.
7. The nail covering system of claim 1, further comprising at least one PMGDM.
8. The nail covering system of claim 1, further comprising a urethane (meth)acrylate.

9. The nail covering system of claim 1, further comprising up to 5 wt % of a plasticizer.

10. The nail covering system of claim 9, wherein said plasticizer is diisobutyl adipate.

11. The nail covering system of claim 1, further comprising up to 10 wt % of a photoinitiator.

12. The nail covering system of claim 11, wherein said photoinitiator is selected from the group consisting of 2,4,6-trimethylbenzoyldiphenylphosphinate, hydroxycyclohexyl phenyl ketone, benzil dimethyl ketal, and mixtures thereof.

13. The nail covering system of claim 1, further comprising up to 10 wt % of a colorant.

14. The nail covering system of claim 13, wherein said colorant is selected from the group consisting of dyes, pigments, effects pigments, and mixtures thereof.

15. The nail covering system of claim 1, comprising a polypropylene glycol (meth)acrylated monomer.

16. The nail covering system of claim 1, comprising a polyethylene glycol (meth)acrylated monomer.

17. The system of claim 1, wherein the non-reactive, solvent-dissolvable polymer and non-reactive solvent are present in sufficient amounts such that, when the coating is cured onto the surface of the nail, the coating cures to an acrylic thermoset lattice layer that is removable from the nail surface within 20 minutes of exposure to organic solvent.

18. The nail covering system of claim 17, wherein the organic solvent is acetone.

19. The nail covering system of claim 1, wherein said at least one non-reactive, solvent-dissolvable polymer is a cellulose ester.

20. The nail covering system of claim 19, wherein said cellulose ester is a cellulose acetate alkylate.

21. The nail covering system of claim 1, wherein said at least one non-reactive solvent is selected from the group consisting of ketones, alkyl acetates, alcohols, alkanes, alkenes, and mixtures thereof.

22. The nail covering system of claim 8, wherein said at least one non-reactive solvent is selected from the group consisting of acetone, ethyl acetate, butyl acetate, isopropyl alcohol, ethanol, methyl ethyl ketone, toluene, hexane, and mixtures thereof.

23. A multilayer system for covering a nail surface comprising:
at least a first layer and a second layer,
wherein at least one of the first layer and the second layer comprises a coating curable to an acrylic thermoset lattice layer conforming over the nail surface upon exposure to actinic radiation, and
wherein the coating comprises
a polymerizable (meth)acrylate,
a polypropylene glycol (meth)acrylated monomer or polyethylene glycol (meth)acrylated monomer,
a non-reactive solvent, and
a non-reactive, solvent-dissolvable polymer.

24. The system of claim 1, wherein the coating when cured comprises an interpenetrating network of the non-reactive solvent-dissolvable polymer.

25. The system of claim 1, wherein the coating when cured comprises an interconnected network of voids.

* * * * *